(12) United States Patent
Hockett et al.

(10) Patent No.: US 8,753,396 B1
(45) Date of Patent: Jun. 17, 2014

(54) INTERVERTEBRAL IMPLANT HAVING BACK-OUT PREVENTION FEATURE

(75) Inventors: Brian E. Hockett, Parma, OH (US); Abid Qureshi, Walnut Creek, CA (US); Steven Lee, Walnut Creek, CA (US); Jeffrey A. Russo, North Canton, OH (US); Peter A. Materna, Metuchen, NJ (US)

(73) Assignee: Theken Spine, LLC, Vista, CA (US)

( * ) Notice: Subject to any disclaimer, the term of this patent is extended or adjusted under 35 U.S.C. 154(b) by 114 days.

(21) Appl. No.: 13/211,872

(22) Filed: Aug. 17, 2011

Related U.S. Application Data

(60) Provisional application No. 61/382,294, filed on Sep. 13, 2010.

(51) Int. Cl.
*A61F 2/44* (2006.01)

(52) U.S. Cl.
USPC ........................................ 623/17.11

(58) Field of Classification Search
USPC .............. 623/17.11–17.16; 606/291; 411/999
See application file for complete search history.

(56) References Cited

U.S. PATENT DOCUMENTS

| | | |
|---|---|---|
| 5,120,171 A | 6/1992 | Lasner |
| 5,258,031 A | 11/1993 | Salib et al. |
| 5,275,601 A | 1/1994 | Gogolewski et al. |
| 5,364,399 A | 11/1994 | Lowery et al. |
| 5,403,136 A | 4/1995 | Mathys |
| 5,520,690 A | 5/1996 | Errico et al. |
| 5,531,554 A | 7/1996 | Jeanson et al. |
| 5,531,746 A | 7/1996 | Errico et al. |
| 5,536,127 A | 7/1996 | Pennig |
| 5,549,612 A | 8/1996 | Yapp et al. |
| 5,578,034 A | 11/1996 | Estes |
| 5,601,553 A | 2/1997 | Trebing et al. |
| 5,616,144 A | 4/1997 | Yapp et al. |
| 5,709,686 A | 1/1998 | Talos et al. |
| 5,876,402 A | 3/1999 | Errico et al. |
| 5,931,838 A | 8/1999 | Vito |
| 5,954,722 A | 9/1999 | Bono |
| 5,964,768 A | 10/1999 | Huebner |
| 6,017,345 A | 1/2000 | Richelsoph |
| 6,030,389 A | 2/2000 | Wagner et al. |
| 6,129,730 A | 10/2000 | Bono et al. |

(Continued)

FOREIGN PATENT DOCUMENTS

| | | |
|---|---|---|
| WO | 9938463 | 8/1999 |
| WO | 9963914 | 12/1999 |
| WO | 0066045 | 11/2000 |
| WO | 0156497 | 8/2001 |

*Primary Examiner* — Nicholas Woodall
(74) *Attorney, Agent, or Firm* — Middleton Reutlinger; Robert H. Eichenberger; Chad D. Bruggeman

(57) ABSTRACT

A spinal implant for implantation in an intervertebral space is provided, such that the implant may provide a back-out prevention feature and may also provide a visual indication of whether the back-out prevention feature is engaged. The visual indication may be a contrast between a circular visible shape of the screw head and a non-circular visible shape of the screw head. The back-out prevention feature may provide engagement of a tapered thread in the screw head with an internal thread of the implant. A hard stop may also be provided. Such back-out prevention feature may also provide a torque-based indication of engagement or non-engagement of the back-out prevention feature. The implant may possess a polymeric posterior body joined to a metallic anterior body.

22 Claims, 16 Drawing Sheets

(56) References Cited

U.S. PATENT DOCUMENTS

| | | |
|---|---|---|
| 6,139,550 A | 10/2000 | Michelson |
| 6,152,927 A | 11/2000 | Farris et al. |
| 6,156,037 A | 12/2000 | LeHuec et al. |
| 6,193,721 B1 | 2/2001 | Michelson |
| 6,224,602 B1 | 5/2001 | Hayes |
| 6,235,059 B1 | 5/2001 | Benezech et al. |
| 6,258,089 B1 | 7/2001 | Campbell et al. |
| 6,273,889 B1 | 8/2001 | Richelsoph |
| 6,306,139 B1 | 10/2001 | Fuentes |
| 6,306,140 B1 | 10/2001 | Siddiqui |
| 6,331,179 B1 | 12/2001 | Freid et al. |
| 6,355,043 B1 | 3/2002 | Adam |
| 6,358,250 B1 | 3/2002 | Orbay |
| 6,364,882 B1 | 4/2002 | Orbay |
| 6,383,186 B1 | 5/2002 | Michelson |
| 6,398,783 B1 | 6/2002 | Michelson |
| 6,413,259 B1 | 7/2002 | Lyons et al. |
| 6,428,542 B1 | 8/2002 | Michelson |
| 6,432,106 B1 | 8/2002 | Fraser |
| 6,440,135 B2 | 8/2002 | Orbay et al. |
| 6,454,769 B2 | 9/2002 | Wagner et al. |
| 6,454,771 B1 | 9/2002 | Michelson |
| 6,458,133 B1 | 10/2002 | Lin |
| 6,527,776 B1 | 3/2003 | Michelson |
| 6,533,786 B1 | 3/2003 | Needham et al. |
| 6,554,863 B2 | 4/2003 | Paul et al. |
| 6,558,423 B1 | 5/2003 | Michelson |
| 6,572,619 B2 | 6/2003 | Santilli |
| 6,575,975 B2 | 6/2003 | Brace et al. |
| 6,585,740 B2 | 7/2003 | Schlapfer et al. |
| 6,599,290 B2 | 7/2003 | Bailey et al. |
| 6,602,255 B1 | 8/2003 | Campbell et al. |
| 6,602,256 B1 | 8/2003 | Hayes |
| 6,616,666 B1 | 9/2003 | Michelson |
| 6,620,163 B1 | 9/2003 | Michelson |
| 6,623,486 B1 | 9/2003 | Weaver et al. |
| 6,626,907 B2 | 9/2003 | Campbell et al. |
| 6,656,181 B2 | 12/2003 | Dixon et al. |
| 6,669,701 B2 | 12/2003 | Steiner et al. |
| 6,695,845 B2 | 2/2004 | Dixon et al. |
| 6,695,846 B2 | 2/2004 | Richelsoph et al. |
| 6,702,817 B2 | 3/2004 | Beger et al. |
| 6,706,046 B2 | 3/2004 | Orbay et al. |
| 6,712,818 B1 | 3/2004 | Michelson |
| 6,716,247 B2 | 4/2004 | Michelson |
| 6,730,090 B2 | 5/2004 | Orbay et al. |
| 6,730,127 B2 | 5/2004 | Michelson |
| 6,749,636 B2 | 6/2004 | Michelson |
| 6,808,537 B2 | 10/2004 | Michelson |
| 6,821,278 B2 | 11/2004 | Frigg et al. |
| 6,866,665 B2 | 3/2005 | Orbay |
| 6,878,167 B2 | 4/2005 | Ferree |
| 6,884,242 B2 | 4/2005 | LeHuec et al. |
| 6,893,444 B2 | 5/2005 | Orbay |
| 6,896,701 B2 | 5/2005 | Boyd et al. |
| 6,916,320 B2 | 7/2005 | Michelson |
| 6,921,403 B2 | 7/2005 | Cragg et al. |
| 6,926,718 B1 | 8/2005 | Michelson |
| 6,936,050 B2 | 8/2005 | Michelson |
| 6,936,051 B2 | 8/2005 | Michelson |
| 6,955,677 B2 | 10/2005 | Dahners |
| 6,962,606 B2 | 11/2005 | Michelson |
| 6,964,664 B2 | 11/2005 | Freid et al. |
| 6,969,390 B2 | 11/2005 | Michelson |
| 6,972,019 B2 | 12/2005 | Michelson |
| 6,984,234 B2 | 1/2006 | Bray |
| 6,986,788 B2 | 1/2006 | Paul et al. |
| 6,989,031 B2 | 1/2006 | Michelson |
| 7,001,389 B1 | 2/2006 | Navarro et al. |
| 7,008,426 B2 | 3/2006 | Paul |
| 7,018,416 B2 | 3/2006 | Hanson et al. |
| 7,033,394 B2 | 4/2006 | Michelson |
| 7,041,105 B2 | 5/2006 | Michelson |
| 7,041,135 B2 | 5/2006 | Michelson |
| 7,044,952 B2 | 5/2006 | Michelson |
| 7,044,953 B2 | 5/2006 | Capanni |
| 7,048,739 B2 | 5/2006 | Konieczynski et al. |
| 7,070,599 B2 | 7/2006 | Paul |
| 7,074,221 B2 | 7/2006 | Michelson |
| 7,087,082 B2 | 8/2006 | Paul et al. |
| 7,097,645 B2 | 8/2006 | Michelson |
| 7,104,991 B2 | 9/2006 | Dixon et al. |
| 7,112,222 B2 | 9/2006 | Fraser |
| 7,128,744 B2 | 10/2006 | Weaver et al. |
| 7,163,561 B2 | 1/2007 | Michelson |
| 7,172,600 B2 | 2/2007 | Beger et al. |
| 7,172,627 B2 | 2/2007 | Fiere et al. |
| 7,175,623 B2 | 2/2007 | Thramann et al. |
| 7,179,260 B2 | 2/2007 | Gerlach et al. |
| 7,182,782 B2 | 2/2007 | Kirschman |
| 7,186,256 B2 | 3/2007 | Michelson |
| 7,204,837 B2 | 4/2007 | Paul |
| 7,229,445 B2 | 6/2007 | Hayeck et al. |
| 7,255,699 B2 | 8/2007 | Paul |
| 7,273,481 B2 | 9/2007 | Lombardo et al. |
| 7,278,997 B1 | 10/2007 | Mueller et al. |
| 7,282,053 B2 | 10/2007 | Orbay |
| 7,288,094 B2 | 10/2007 | Lindemann et al. |
| 7,288,095 B2 | 10/2007 | Baynham et al. |
| 7,300,465 B2 | 11/2007 | Paul et al. |
| 7,306,605 B2 | 12/2007 | Ross |
| 7,309,340 B2 | 12/2007 | Fallin et al. |
| 7,311,712 B2 | 12/2007 | Dalton |
| 7,322,983 B2 | 1/2008 | Harris |
| 7,322,984 B2 | 1/2008 | Doubler et al. |
| 7,341,589 B2 | 3/2008 | Weaver et al. |
| 7,347,873 B2 | 3/2008 | Paul et al. |
| 7,354,441 B2 | 4/2008 | Frigg |
| 7,399,301 B2 | 7/2008 | Michelson |
| 7,442,209 B2 | 10/2008 | Michelson |
| 7,527,640 B2 | 5/2009 | Ziolo et al. |
| 7,608,107 B2 | 10/2009 | Michelson |
| 7,637,928 B2 | 12/2009 | Fernandez |
| 7,691,133 B2 | 4/2010 | Partin et al. |
| 7,695,472 B2 | 4/2010 | Young |
| 7,695,502 B2 | 4/2010 | Orbay et al. |
| 7,699,880 B2 | 4/2010 | Orbay et al. |
| 7,704,279 B2 | 4/2010 | Moskowitz et al. |
| 7,722,653 B2 | 5/2010 | Young et al. |
| 7,736,380 B2 | 6/2010 | Johnston et al. |
| 7,740,648 B2 | 6/2010 | Young et al. |
| 7,780,732 B2 | 8/2010 | Abernathie |
| 7,794,502 B2 | 9/2010 | Michelson |
| 7,846,207 B2 | 12/2010 | Lechmann et al. |
| 7,875,076 B2 | 1/2011 | Mathieu et al. |
| 7,942,903 B2 | 5/2011 | Moskowitz et al. |
| 7,963,982 B2 | 6/2011 | Kirschman |
| 7,972,363 B2 | 7/2011 | Moskowitz et al. |
| 7,985,255 B2 | 7/2011 | Bray et al. |
| 8,057,548 B2 | 11/2011 | Abernathie et al. |
| 8,100,976 B2 | 1/2012 | Bray et al. |
| 8,268,000 B2 | 9/2012 | Waugh et al. |
| 8,273,127 B2 | 9/2012 | Jones et al. |
| 8,328,872 B2 | 12/2012 | Duffield et al. |
| 2002/0193880 A1 | 12/2002 | Fraser |
| 2005/0085913 A1 | 4/2005 | Fraser et al. |
| 2005/0192578 A1 | 9/2005 | Horst |
| 2006/0085071 A1 | 4/2006 | Lechmann et al. |
| 2006/0241763 A1 | 10/2006 | Paul et al. |
| 2007/0250167 A1 | 10/2007 | Bray et al. |
| 2008/0046090 A1 | 2/2008 | Paul et al. |
| 2008/0177307 A1 | 7/2008 | Moskowitz et al. |
| 2008/0249625 A1 | 10/2008 | Waugh et al. |
| 2008/0312742 A1 | 12/2008 | Abernathie |
| 2009/0024170 A1* | 1/2009 | Kirschman ............ 606/280 |
| 2009/0062921 A1 | 3/2009 | Michelson |
| 2009/0105830 A1 | 4/2009 | Jones et al. |
| 2009/0270926 A1 | 10/2009 | Hawkes |
| 2010/0057206 A1 | 3/2010 | Duffield et al. |
| 2010/0087925 A1* | 4/2010 | Kostuik et al. ......... 623/17.16 |
| 2010/0312285 A1* | 12/2010 | White et al. ............ 606/289 |
| 2011/0251689 A1 | 10/2011 | Seifert et al. |

* cited by examiner

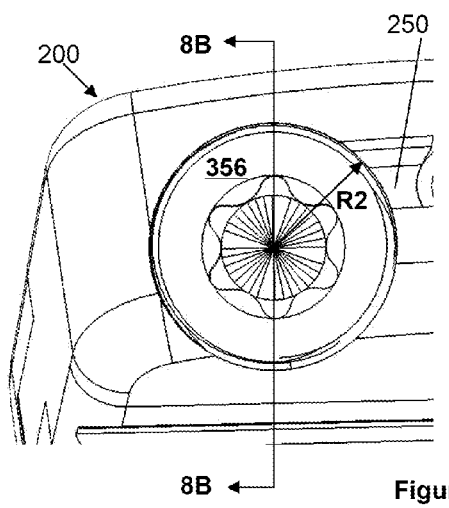
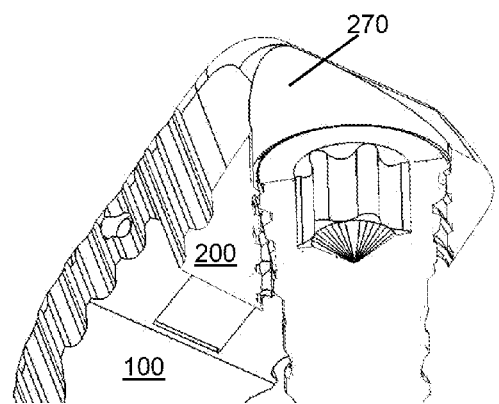
Figure 8A                Figure 8B
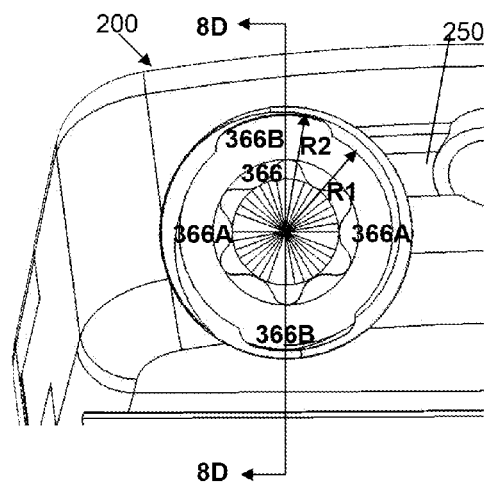
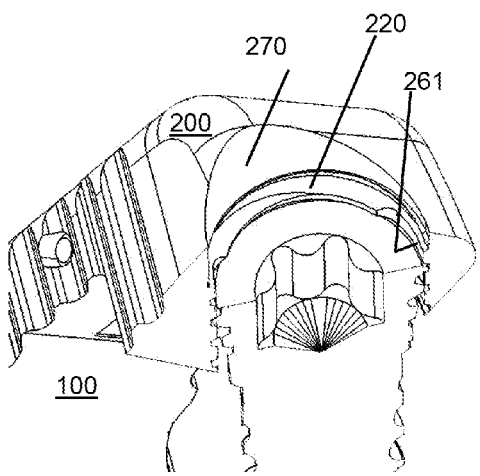
Figure 8C                Figure 8D

INTERVERTEBRAL IMPLANT HAVING BACK-OUT PREVENTION FEATURE

CROSS-REFERENCE TO RELATED APPLICATION

This application claims priority to and benefit under 35 U.S.C. §119(e) to U.S. Provisional App. No. 61/382,294, entitled Intervertebral Implant having Back-Out Prevention Feature, and filed on Sep. 13, 2010. The entire contents of the aforementioned application are herein incorporated by reference.

TECHNICAL FIELD

Embodiments of the invention pertain to spinal surgery.

BACKGROUND

Spinal surgery may involve spinal fusion, and intervertebral space for implants may be very limited, especially in the cervical region.

SUMMARY

In a first embodiment, there is provided a spinal cage-plate having a screw back-out prevention feature in which the engagement or non-engagement of the mechanism may be visually observable by shape of what is visible of a head of a screw. The observable shape during non-engagement may be circular, and the observable shape during engagement may be non-circular.

In another embodiment, there is provided a spinal cage-plate having a screw back-out prevention feature in which the engagement or non-engagement of the mechanism may be visually observable by shape of what is visible of a head of a screw. It is possible that the observable shape during non-engagement is a shape that has indentations (i.e., is non-circular), and the observable shape during engagement is circular.

In another embodiment, the screw has a first threaded portion for engagement with bone, and a second threaded portion that engages with an anterior body of the implant with the threaded portions having different thread pitches and with the threaded portion on the screw head being tapered.

In yet another embodiment, engagement of a back-out prevention feature may be observable both by an increase in torque required to drive the screw and by a visual indication.

Yet another embodiment provides a screw having a lip that interacts with certain features of the implant to provide hard stop when the screw has been inserted to a predetermined point.

Another embodiment provides a spinal surgical device possessing an implant suitable to fit in an intervertebral space between adjacent vertebrae. The implant may be provided with a hole therethrough suitable to accept a screw. At least a portion of the hole may have an internal helical thread. The hole may further be provided with an interior envelope that is non-circular.

Another embodiment provides spinal surgical device having an implant suitable to fit in an intervertebral space between adjacent vertebrae. The implant may be provided with a hole therethrough with the hole having a hole internal thread. A screw may be provided that is suitable to pass through the hole and has a threaded shaft suitable to engage bone of one of the adjacent vertebrae and may further have a head larger in diameter than a shaft of the screw. The screw provides, upon engagement of a back-out prevention feature, both an indication in terms of increased torque to advance the screw and a visual indication of engagement.

Another embodiment provides spinal surgical device having an implant suitable to fit in an intervertebral space between adjacent vertebrae. The implant may be provided with a hole therethrough. A screw may also be provided to pass through the hole. The hole may possess an internal thread and the screw may have a screw head. Interaction between the screw and the implant may provide a back-out prevention feature for preventing the screw from backing out of the implant. The interaction between the screw and implant may also provide a visual indication of engagement of the back-out feature. The visual indication may display a change in a shape of a visible portion of the screw head when the back-out prevention feature is engaged as compared to a shape of a visible portion of the screw head when the back-out prevention feature is not engaged.

Another embodiment provides spinal surgical device having an implant suitable to fit in an intervertebral space between adjacent vertebrae. The implant may be provided with a hole therethrough and the hole may be provided with an internal thread. The embodiment may also be provided with a screw suitable to pass through the hole. A combination of the implant and screw may provide a back-out prevention feature for preventing the screw from backing out of the implant. The back-out prevention feature may provide both a visual indication of engagement of the back-out prevention feature and a torque indication of the back-out prevention feature. The visual indication may display a change of a visible shape of the screw head, and the torque indication may display a change in an amount of torque needed to advance the screw.

Another embodiment provides spinal surgical device having an implant suitable to fit in an intervertebral space between adjacent vertebrae. The implant may be provided with a hole therethrough and the hole may be provided with an internal thread. The embodiment may also be provided with a screw suitable to pass through the hole. The screw may also have a screw head that is substantially rigid. An interaction between the implant and screw may provide a back-out prevention feature for preventing the screw from backing out of the implant. The interaction between the implant and screw may provide a visual indication of engagement of the back-out prevention feature. During non-engagement of the back-out prevention feature, the screw head may be visible in its entirety, and the screw head may have an external periphery that is not perfectly circular. Upon engagement of the back-out prevention feature, a visible portion of the screw head is substantially circular.

BRIEF DESCRIPTION OF THE ILLUSTRATIONS

Embodiments of the invention are further described in the following illustrations.

FIG. 8A is a perspective view of the screw head and the anterior body in a not-fully-engaged condition.

FIG. 8B is a partial cross-section of the embodiment shown in FIG. 8A.

FIG. 8C is a perspective view of the screw head and the anterior body in a fully-engaged condition.

FIG. 8D is a partial cross-section of the embodiment shown in FIG. 8C.

DETAILED DESCRIPTION

Figure 1:
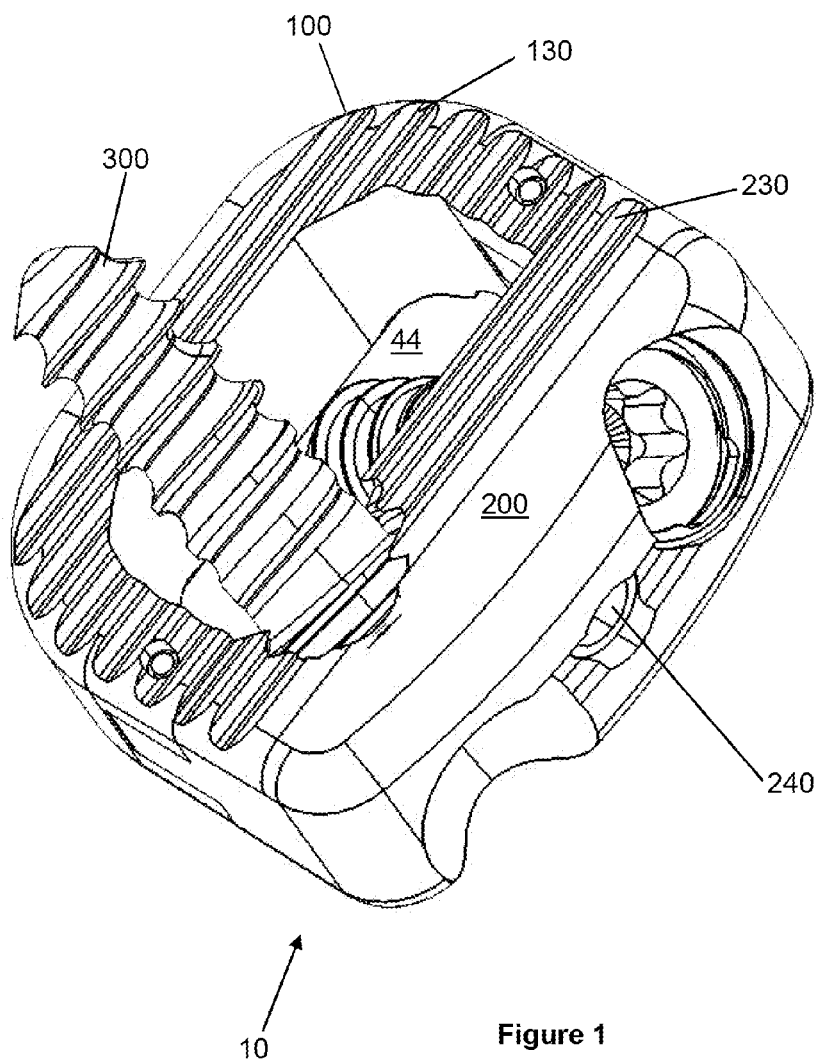
FIG. 1 is a perspective view of an implant assembly.
Figure 2A:
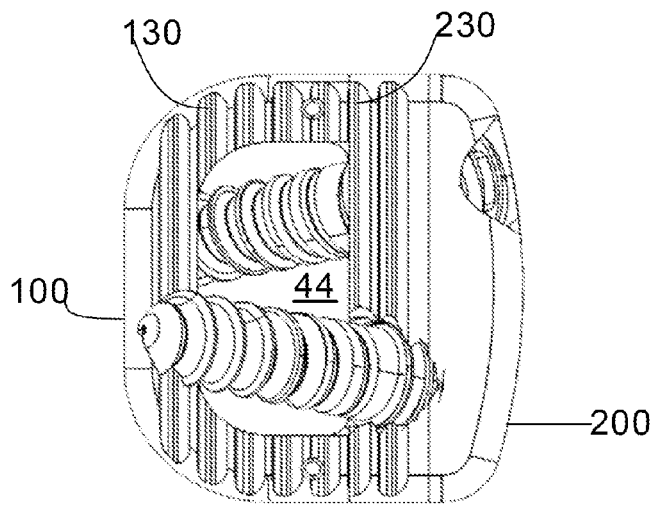
FIG. 2A is a top view of the assembly shown in FIG. 1.
Figure 2B:
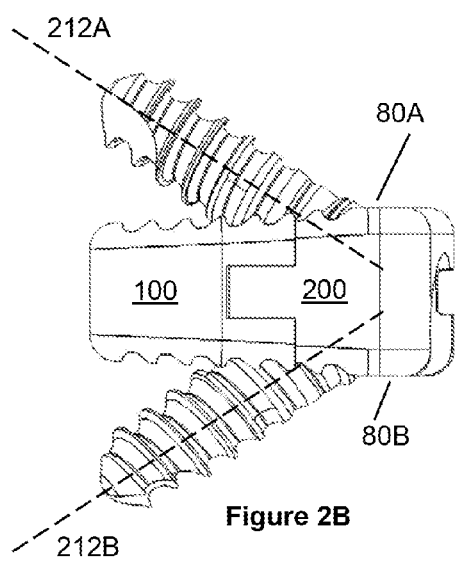
FIG. 2B is a side (lateral) view of the assembly shown in FIG. 1.
Figure 2C:
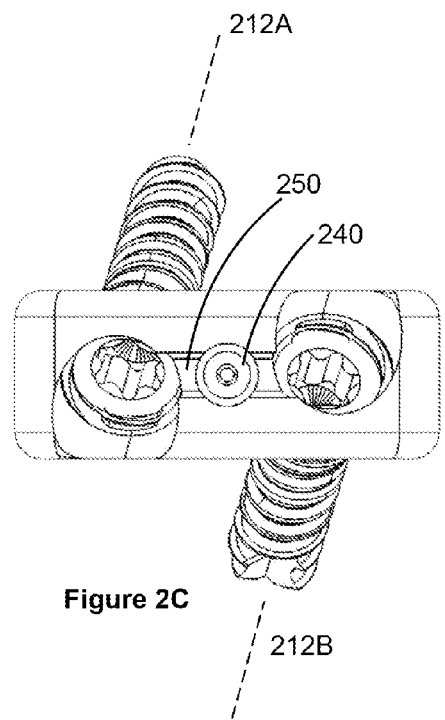
FIG. 2C is a front view of the assembly shown in FIG. 1.

The disclosed embodiments may further be understood with reference to FIG. 1 and to FIGS. 2a, 2b and 2c. An embodiment is provided with an implant 10 that has a posterior body 100 and an anterior body 200 connected to each other. It can be understood that the designations anterior and posterior are only for purposes of description.

The posterior body 100 and the anterior body 200 may fit together. For example, one or the other of the posterior body 100 and the anterior body 200 may have a male feature and the other may have a complementary female feature. The posterior body 100 and the anterior body 200 may fit together such that, together, they form an implant 10 that has an outside perimeter and encloses an open space 44 in the interior of the implant 10. The outside perimeter of the implant 10 may be smaller than, or approximately equal to, the enveloping outline of an intervertebral disc. The open interior space 44 of implant 10 may be suitable to receive bone graft or bone growth promoting material or other material, in any combination desired by a surgeon.

The combination of the posterior body 100 and the anterior body 200 may have a first end face 80a and a second end face 80b opposed to the first end face 80a. Either or both of these end faces 80a, 80b may possess grooves 130, 230 (as illustrated in FIG. 1), or alternatively, teeth, roughness or other similar features to discourage sliding or displacement of the assembly relative to adjacent vertebrae. The grooves 130, 230 in the first end face 80a may be substantially parallel to the grooves 130, 230 in the second end face 80b. The end faces 80a, 80b may each have respective enveloping planes. The respective enveloping planes may be parallel to each other, or may be non-parallel to each other so as to provide a desired degree of lordosis.

The anterior body 200 may have two screw-holes 210a, 210b therethrough, suitable to receive screws. There may further be provided two screws (not shown in FIG. 3 or 4) that pass through the holes 210a, 210b in the anterior body 200.

Figure 3:
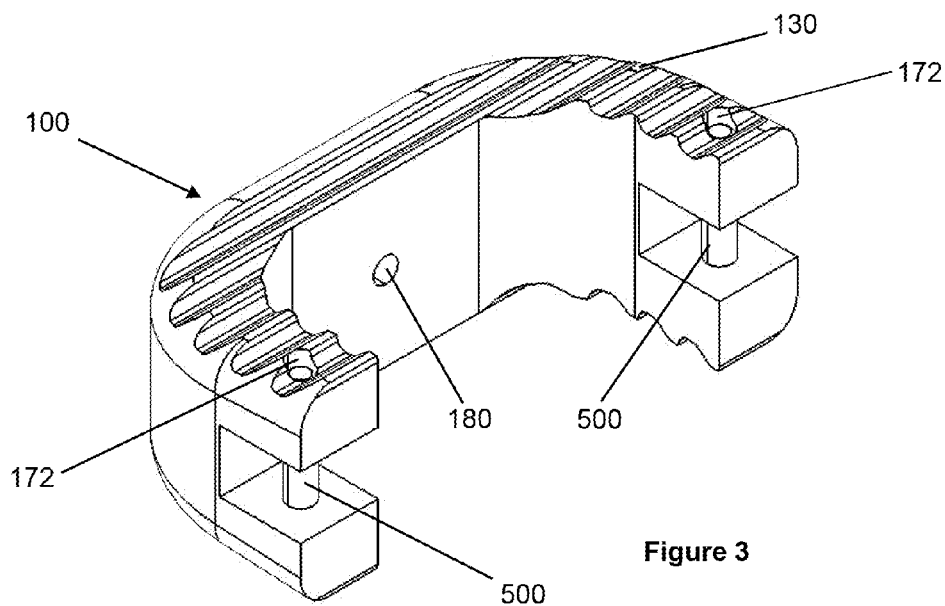
FIG. 3 is a perspective view of the posterior body of the assembly shown in FIG. 1.
Figure 4:
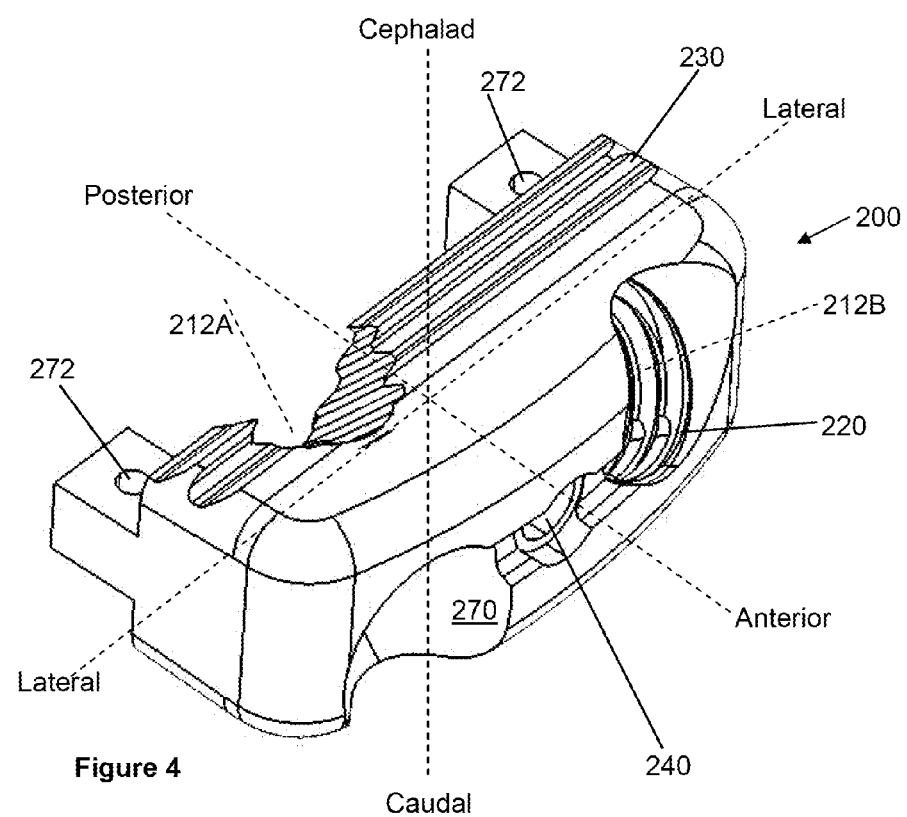
FIG. 4 is a perspective view of the anterior body of the assembly shown in FIG. 1.

With additional reference to FIGS. 3 and 4, the screw holes 210a, 210b (not shown in FIG. 3 or 4) may have respective screw hole axes 212a, 212b, and may be symmetrically located with respect to a central plane of symmetry of the implant 10. The orientation of the screw holes 210a, 210b may be such that when the implant 10 is viewed from the side, as in FIG. 2b, the screws 300a, 300b and the screw hole axes 212a, 212b point away from each other such that one screw hole axis 212a points toward a first vertebra and a second screw hole axis 212B points toward a second vertebra that is different from and adjacent to the first vertebra. The orientation of screw-holes 210a, 210b may be such that when the implant 10 is viewed from the top, as in FIG. 2a, the screw hole axes 212a, 212b point slightly toward each other. However, alternatively, it would also be possible for the screw hole axes 212a, 212b, as viewed in FIG. 2a, to be located in planes are parallel to each other, or the screw hole axes 212a, 212b could have still other orientations.

In addition to the screw-holes 210a, 210b, the anterior body 200 may further possess a central hole 240 that may be appropriate for interface with an installation instrument or for use for other purposes. The anterior body 200 may further possess an external groove 250 that also may be appropriate for interface with an installation instrument. The Central hole 240 may be appropriately sized and oriented so as to permit injection of a substance therethrough or passage of a syringe therethrough.

As shown in FIG. 3, there is illustrated a posterior body 100 in isolation, and also showing dowel pins 500. The dowel pins 500 may form an interference fit with respect to the corresponding holes 172 in the posterior body 100. Alternatively, the dowel pins 500 may be a clearance fit with respect to the corresponding holes 172 in the posterior body 100.

The posterior body 100 may have, on its cephalad-facing surface and on its caudal-facing surface, grooves 130 or ridges suitable to engage with bone 50. Such grooves 130 may be non-symmetric such that they may have a preferred direction so that inserting implant 10 into position in the surgical site is easier than withdrawing implant 10 from the surgical site. Alternatively, other forms of surface irregularity could be used on the cephalad-facing and caudal-facing surface of posterior body 100.

The posterior body 100 may be provided with a radiopaque marker that may be a metallic pin press-fitted into a corresponding hole 180 in the posterior body 100. As illustrated, such a pin may be located in one or more planes of symmetry of the posterior body 100. The posterior body 100 may be made of, or possess, a polymer such as polyetheretherketone (PEEK).

With respect to FIG. 4, the anterior body 200 is illustrated in isolation. The anterior body 200 and the posterior body 100 need not be made of the same material. For example, the anterior body 200 may be made of a biocompatible metal such as titanium or a titanium alloy. The use of a metal for the anterior body 200 may be suitable for the formation of internal threads and similar load-bearing features in the anterior body 200. The anterior body 200 may have an anterior face and a posterior face, two lateral sides, and a cephalad direction or axis and a caudal direction or axis. It may be understood that these directions or axes are for descriptive purposes only.

Regarding connection between the posterior body 100 and the anterior body 200, there may be collinear holes through the posterior body 100 and the anterior body 200, suitable to receive the dowel pin 500. As stated, the dowel pin 500 may be either an interference fit or a clearance fit with hole 272 in anterior body 200. The dowel pin 500 may be provide an interference-fit in one or the other of the posterior body 100 and the anterior body 200, and may be a clearance fit in the other of the posterior body 100 and the anterior body 200. Dowel pins 500 may be provided at each of two locations in the overall assembly. Details of the interference fit or clearance fit may be identical on the two opposite sides of the assembly, or alternatively they could be different. The dowel pins 500 may be radiopaque.

There are various possibilities regarding the fit of the dowel pin 500 with neighboring structures. The dowel pin 500 may form an interference fit with the corresponding holes in the anterior body 200, and may form a clearance fit with the corresponding holes in the posterior body 100. Another possibility is that the dowel pin 500 may form an interference or friction fit with the corresponding holes in posterior body 100, and may form a clearance fit with the corresponding holes in the anterior body 200. In either of these situations, it is possible that there could be slight looseness in the joint between the posterior body 100 and the anterior body 200. Alternatively, it is possible that the dowel pins 500 may form an interference fit both with the corresponding holes 172 in the posterior body 100 and with the corresponding holes 272 in the anterior body 200. In such a configuration, there might be no looseness in the joint between the posterior body 100 and the anterior body 200.

The anterior body 200 may have, on its cephalad-facing surface and on its caudal-facing surface, grooves suitable 230 to engage with bone 50. Such grooves 230 may be non-symmetric such that they may have a preferred direction so that inserting implant 10 into position in the surgical site is easier than withdrawing implant 10 from the surgical site. Alternatively, other forms of surface irregularity could be used on the cephalad-facing and caudal-facing surface of the anterior body 200.

Details of the holes 210a, 210b through the anterior body 200 are illustrated in FIGS. 4, 5A, 5B, and 5C. The anterior body 200 may have a first hole 210a and a second hole 210b therethrough, with those holes having a respective first axis 212a and a second axis 212b. The first axis 212a and the second axis 212b may be skew with respect to each other, i.e., not coplanar and not intersecting each other. The first hole 210a may be to the left of anterior-posterior midplane and the second hole 210B may be to the right of the midplane. As illustrated, the first hole axis 212A may point (looking posteriorly) partially in a cephalad direction, and the second hole axis 212B may point (looking posteriorly) partially in a caudal direction.

Figure 5A:
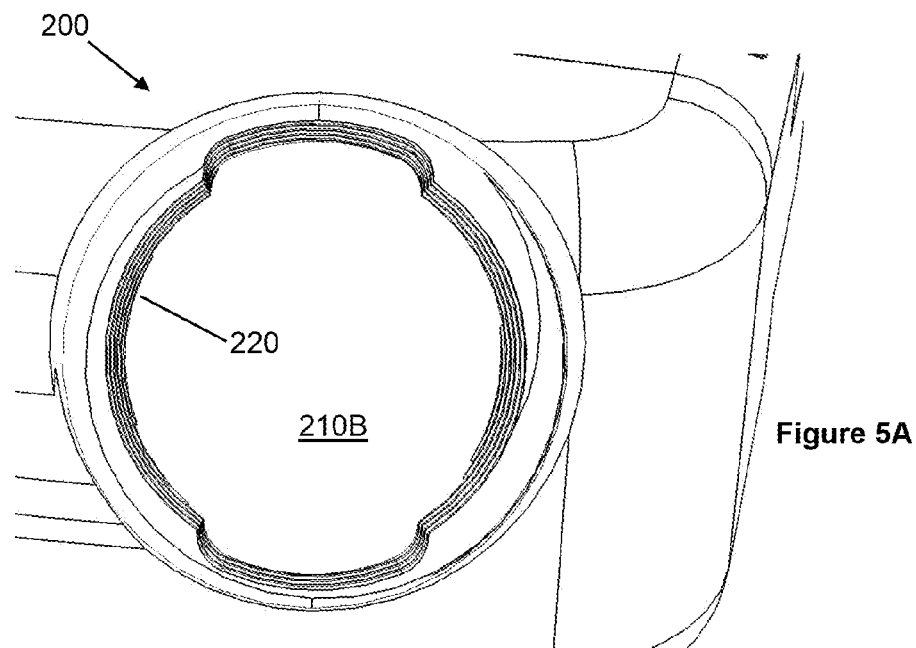
FIG. 5A is a perspective view of one of the holes in the anterior body, viewed nearly along the hole axis.
Figure 5B:
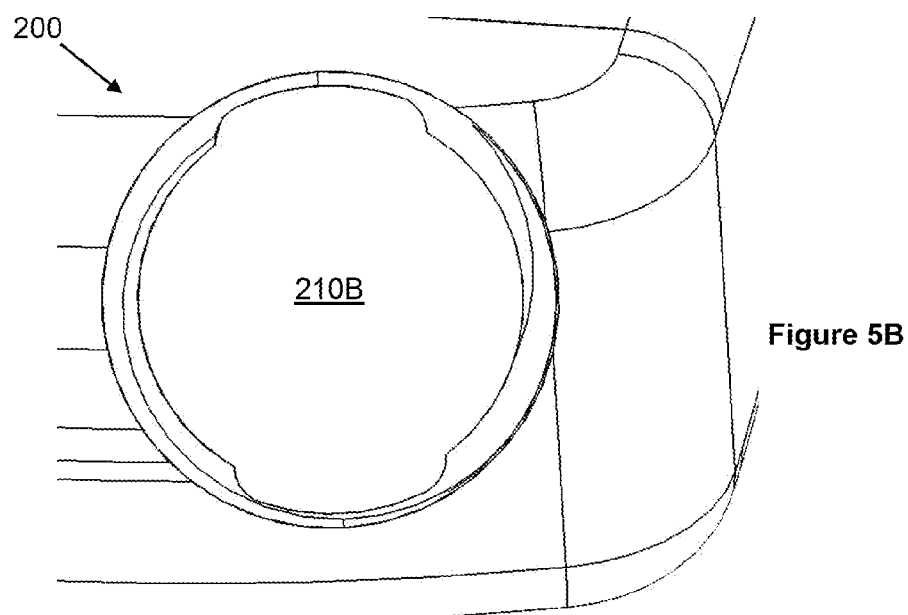
FIG. 5B is an orthographic view of one of the holes in the anterior body, viewed nearly along the hole axis.

Referring now to FIGS. 5A-6B, there are shown close-up views of anterior body 200 in the immediate vicinity of the hole 210B. Both FIGS. 5A and 5B are views approximately along the axis 212B o the f hole 210B.

The screw hole 210A, 210B through the anterior body 200 may, as illustrated, be a hole with an internal helical thread 220. The thread 220 may have uniform thread characteristics along the entire threaded length. Of course, alternatively, it is also possible that the threads 220 of threaded hole 210A, 210B could be non-uniform in some sense. For example the threads 220 may be of a constant pitch everywhere but could be tapered such that there is a larger opening dimension at the anterior face of the anterior body 200 and a smaller opening dimension away from the anterior face of the anterior body 200.

Figure 6A:
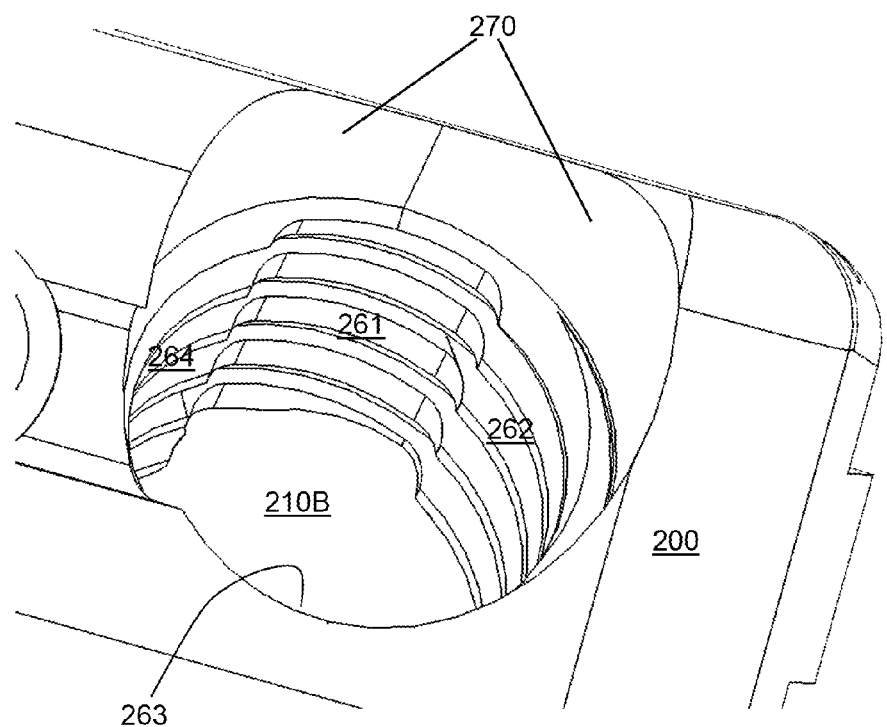
FIG. 6A is a perspective view of one of the holes in the anterior body, viewed off-axis, illustrating one perimeter region being recessed relative to another perimeter region.

With reference to FIG. 6A, in addition to the described internal thread 220, the holes 210A, 210B may also contain an entry region 270 that may be located adjacent to the thread 220 and be located closer to the front (anterior) surface of the anterior body 200 than is the thread 220. Such an entry region 270 may be unthreaded, such as a simple cylindrical hole that has an internal diameter that is larger than the root diameter of the hole 210A, 210B adjacent to the threads 220. Alternatively, it is possible that the entry region 270 may be a chamfer of any desired chamfer angle, while again lying at a radial position larger than the radius of the root of the thread 220.

Figure 5C:
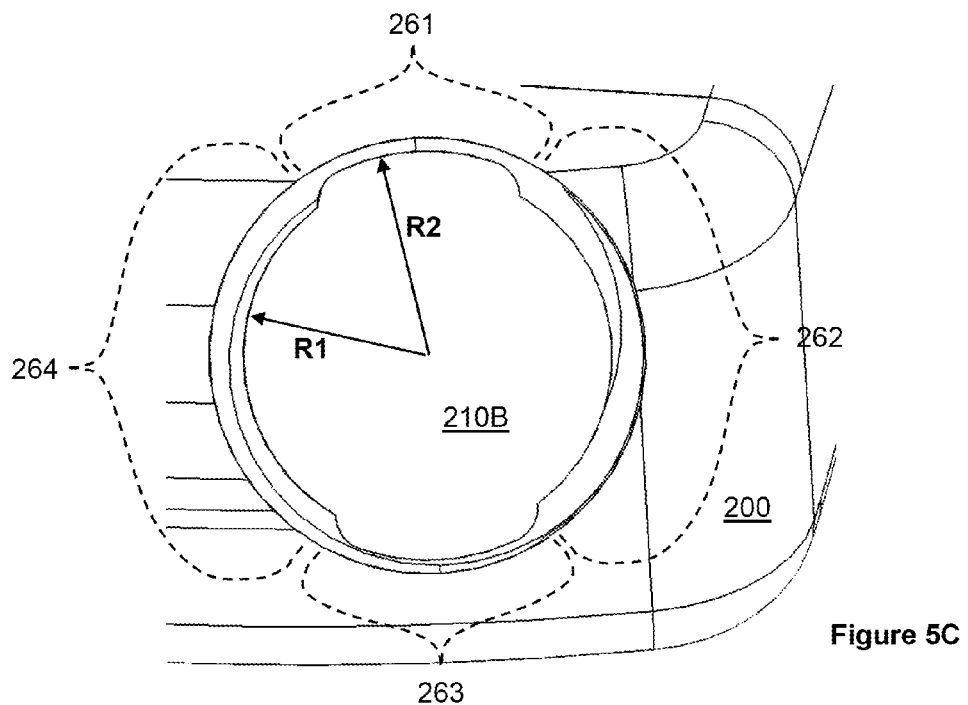
FIG. 5C is a similar view to that of FIG. 5B

As best illustrated in FIGS. 5C and 6A, the perimeter of the hole 210A, 210B may possess four perimeter regions 261, 262, 263, 264 in sequence around the perimeter. The perimeter regions 261 and 263 may be opposed to each other, and the perimeter regions 262 and 264 may be opposed to each other. There may be a common helical thread that runs through all of the perimeter regions 261, 262, 263, 264. However, these four perimeter regions 261, 262, 263, 264 may not all be identical to each other. Rather, some of these perimeter regions, such as 262, 264, may have threads that have a thread profile that is relatively full, while other perimeter regions, such as 261, 263, may have threads that are abbreviated in a radial direction, with the boundary of the perimeter regions 261, 263 being at a radially larger location than the boundary of the perimeter regions 262, 264.

As illustrated, in this view it can be seen that perimeter regions 261 and 263 are recessed such that a partial amount of the thread 220 is removed, but the removal does not extend all the way to the root of the thread 220. In other words, the helical thread 220 is continuous, but at recessed perimeter regions 261, 263 the thread is partial. In contrast at the perimeter regions 262, 264, the thread is full or at least is fuller than in perimeter regions 261, 263. Of course, alternatively, it would also be possible that in recessed perimeter regions 261, 263 the thread could be completely removed. It is believed, although it is not wished to be limited to this explanation, that the presence of a partial thread in the recessed perimeter regions 261, 263 helps to reduce the possibility of cross-threading of a screw into hole 210A, 210B, compared to the possibility of cross-threading if the thread were completely absent in the recessed perimeter regions 261, 263.

Figure 6B:
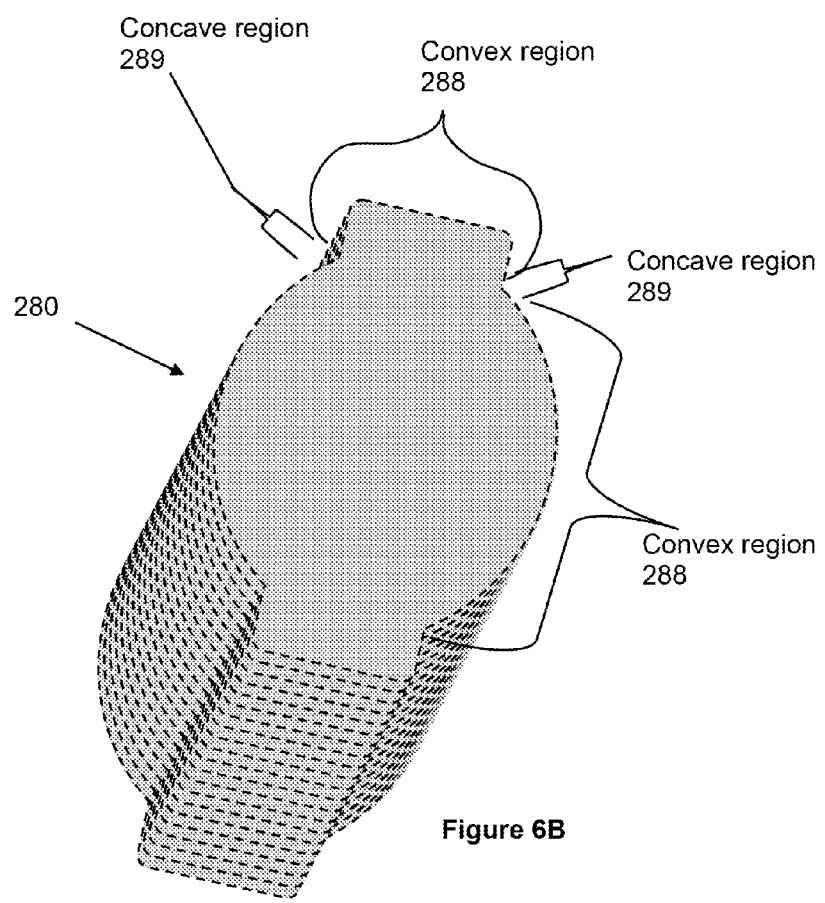
FIG. 6B illustrates a hypothetical enveloping shape that displays the shape of the empty space within a portion of one of the holes in the anterior body.

As further illustration of the described geometry, FIG. 6B illustrates a hypothetical envelope 280 of the space that is the interior of the threaded region 220 of the hole 210A, 210B. The dashed lines in FIG. 6B are simply to help illustrate the shape. This envelope 280 ignores the details of the threads 220 themselves and essentially indicates the envelope of space if the thread 220 was filled in or smoothed over; it can be considered that the illustrated envelope shape 280 connects the crests of the threads 220. It can be observed that the cross-section of this envelope 280 is non-circular and is different from the shape of the head of the screw 300. The screw head 322 would typically be circular although other shapes are possible. More descriptively, the cross-section of the envelope shape 280 contains, viewed from the exterior of this envelope shape 280, both convex regions 288 and concave regions 289.

Figure 7A:
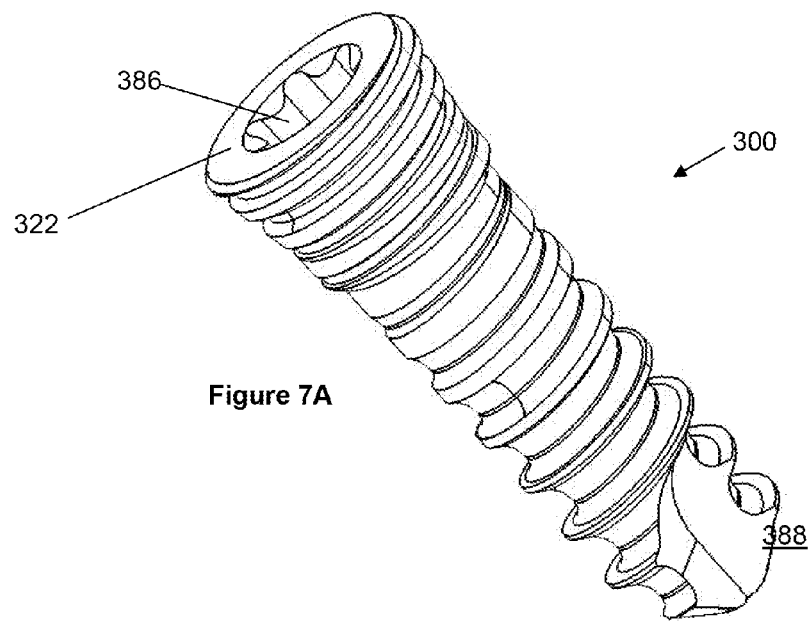
FIG. 7A is a perspective view an embodiment of a screw.
Figure 7B:
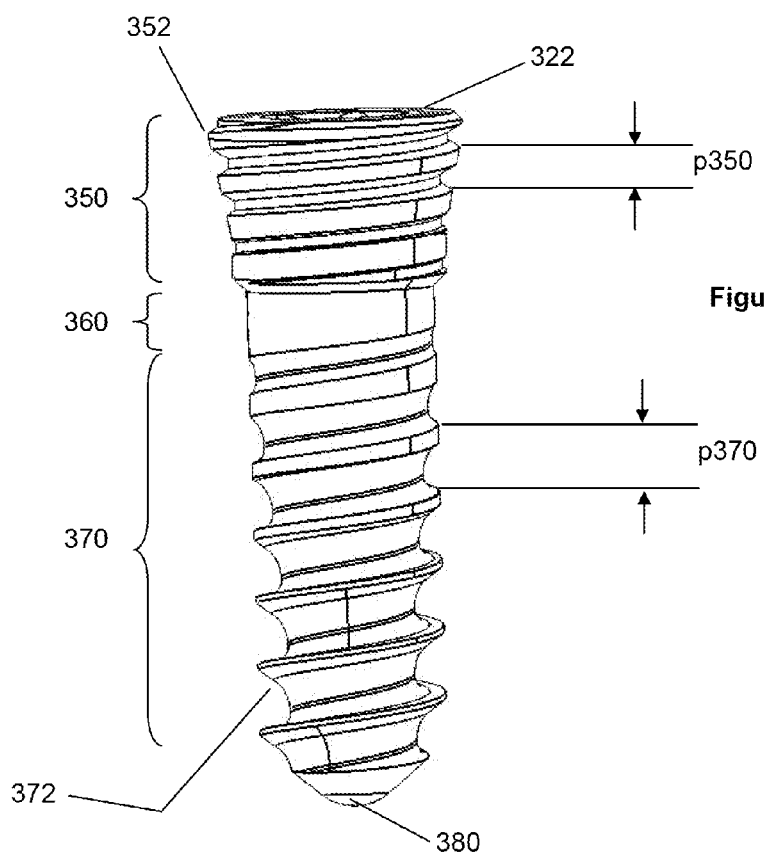
FIG. 7B is a side view of the screw shown in FIG. 7A.

Referring now to FIG. 7A and FIG. 7B, there are illustrated aspects of the screw 300. The screw 300 may have a first threaded region 350 and a second threaded region 370. It is also possible that there may be an unthreaded region 360 between the first threaded region 350 and the second threaded region 370. However, the unthreaded region 360 is not essential. The screw 300 may also have a tip region 380 that comes to a point. The screw 300 may further be provided with a tool interface feature 386, such as a hexalobe feature, in the head of the screw 300, and may further possess a thread interruption 388 near the tip 380 so as to make the screw 300 able to self-tap into bone 50.

As illustrated, in the second threaded region 370, over at least most of the length of the second threaded region 370, the crest of the thread 372 is at an approximately constant radial dimension, but the root of the thread 372 lies along a taper. Of course, other thread profiles are also possible. The unthreaded region 360 typically would be approximately cylindrical. In first threaded region 350, as illustrated, both the root and the crest of the thread 352 may be tapered along a longitudinal axis of screw 300, the first threaded region 350 may be shorter than the second threaded region 370. However, for all of these threads and regions, there are also other possibilities regarding the details of the threads.

The thread pitch of any external thread may be defined as the distance, measured generally along an axial direction of the screw thread, from a first radially-outermost point to a second radially-outermost point that is exactly one rotation (360 degrees) away from the first radially-outermost point. In various embodiments, the first threaded region 350 may have a first thread pitch labeled in FIG. 7B as p350, and the second threaded region 370 may have a second thread pitch labeled in FIG. 7B as p370. The thread pitch p370 on the bone-engaging second threaded region 370 of the screw may be larger than the thread pitch p350 on the locking portion first threaded region 350 of the screw. For example, the second threaded region (bone-engaging portion) 370 of the screw may have a thread pitch of 1.25 mm, while the first threaded region (locking portion) 350 of the thread may have a thread pitch of 32 threads per inch, i.e., 0.8 mm.

As a result of the existence of two different thread pitches on different thread regions 350, 370 of the screw 300, when the screw 300 is being rotated in an advancing direction of rotation at a time when both the bone-engaging thread 372 engages bone 50 and the locking thread 352 engages the thread 220 in the anterior body 200, the screw 300 may act to pull bone 50 into closer contact with the implant 10.

The first threaded region 350, which may be tapered, may have dimensions appropriate so that when the screw 300 is sufficiently far advanced into the anterior body 200, there is some geometric interference between the screw threads 352 and the internal threads 220 of the anterior body 200. This interference may create a frictional restraint which discourages screw 300 from backing out of the implant 10 and of bone 50.

In another embodiment, the interrelationship between the various parts, such as anterior body 200 and screw 300, may be such that it requires a moderate amount of torque to advance the screw 300 into bone 50 when the threads 352 are not engaged with the anterior body 200, but when the threads 352 are engaged with the internal threads 220 of the anterior body 200, the required torque increases noticeably. The initial torque may be associated with friction of the threads 372 against bone material 50. The increased torque may be associated with the interaction of the tapered threads 352 with the internal threads 220 in the anterior body 200. This interaction may provide a frictional restraint to discourage the screw 300 from backing out of the anterior body 200 and of bone 50, which may serve as a back-out prevention or secondary locking means.

The entry region 270 may be dimensioned so as to "hide" the head of the screw 300 within the envelope of the anterior body 200, i.e., so that the head of the screw 300 does not protrude beyond an envelope or outline of the anterior body 200. This may help to avoid irritating soft tissue in the patient's body. Also, as illustrated later herein, the presence of an entry region 270 may also help to emphasize the visual distinction of full engagement versus partial engagement, because at every point around the circumference there will be anterior body material available to contribute to the appearance. However, an entry region 270 is not essential.

The interaction of the various described features may be such as to provide a visual indication of when the screw 300 is sufficiently far advanced into the anterior body 200 to achieve geometric interference suitable to provide prevention of screw back-out. In order to accomplish this, there may be a specified relationship between the dimensions of the thread 220, the thread 352, dimensions of features such as the entry region 270, and the dimensions and location of the head of the screw 300, and other parameters, so that friction and tightness and possible geometric interference begin to occur around the time that the head of the screw 300 has just begun to pass beyond the start point of the thread 220.

Referring now to FIGS. 8A-8D, there are shown two different configurations and appearances of the screw head and nearby material of the anterior body 200, so as to provide a visual difference between the appearance of a fully-inserted screw configuration and the appearance of a partially-inserted configuration.

In the partially-inserted configuration shown in FIG. 8A, the visible region 356 may be substantially circular and may have a radius R2 to its edge. As better illustrated in FIG. 8B, the screw 300 is positioned such that screw head 322 has not yet entered the thread 220 and therefore the screw head 322 is in entry region 270 and thus the entire screw head 322 is visible, in this case, as a circular shape. In this configuration, the screw thread 352 of the threaded region 350 is only loosely engaged, if engaged at all, with the corresponding portion of thread 220.

In the fully-inserted configuration shown in FIG. 8C, the visible region 366 may be generally non-circular and may resemble the cross-sectional shape of the envelope shape 280. In this configuration, the screw thread 352 of the threaded region 350 is tightly engaged with the corresponding portion of the thread 220. In FIG. 8D it can be seen that the entire head 322 of the screw 300 has already entered the thread 220, and therefore the appearance of the head 322 is determined in part by the presence of the thread 220. FIG. 8D, although being a cross-section of the embodiment shown in FIG. 8C, is shown viewed at an angle fairly far from head-on, in order to better illustrate the presence of the recessed perimeter region 261 and to better illustrate how the non-circular visible shape of the screw head 322 is achieved for this situation. The visible region 366 may include, at various different angular positions, a compact portion 366a (in two places, as illustrated) and an expanded portion 366b (in two places, as illustrated). The compact portion 366a may be bounded by circular arcs having a radius R1. The expanded portion 366b may include a region located at a radial location greater than radius R1. The expanded portion 316b may itself be bounded by a circular arc having a radius R2, with radius R2 being greater than radius R1. However, it is not essential that the outer boundary of the expanded portion 316b actually be a circular arc; other shapes are also possible as long as they include material located at a radial location greater than radius R1. It is also possible that the quantity of each region (366a, 366b) could be as few as one, or could be greater than two. It is also possible that the boundary of the compact portion 366a could be something other than a circular arc. It also is possible that the boundary of the expanded portion 366b could be something other than a circular arc. In contrast to FIG. 8A, FIG. 8C is such that the perimeter of observed shape 366 contains places at which two segments of the perimeter meet at a sharp corner, i.e., a fairly abrupt change. Also, the observed shape 366, as viewed from its exterior contains some convex portions and some concave portions (in this case, the corners being the concavities). This corresponds to the description given in connection with envelope 280 in FIG. 6B.

The presence of such a fairly distinct change of shape can make it relatively easy to visually distinguish between the engaged condition and the non-engaged condition of the back-out prevention feature. Still other geometries of the visible shape are also possible as discussed elsewhere herein.

Figure 9:
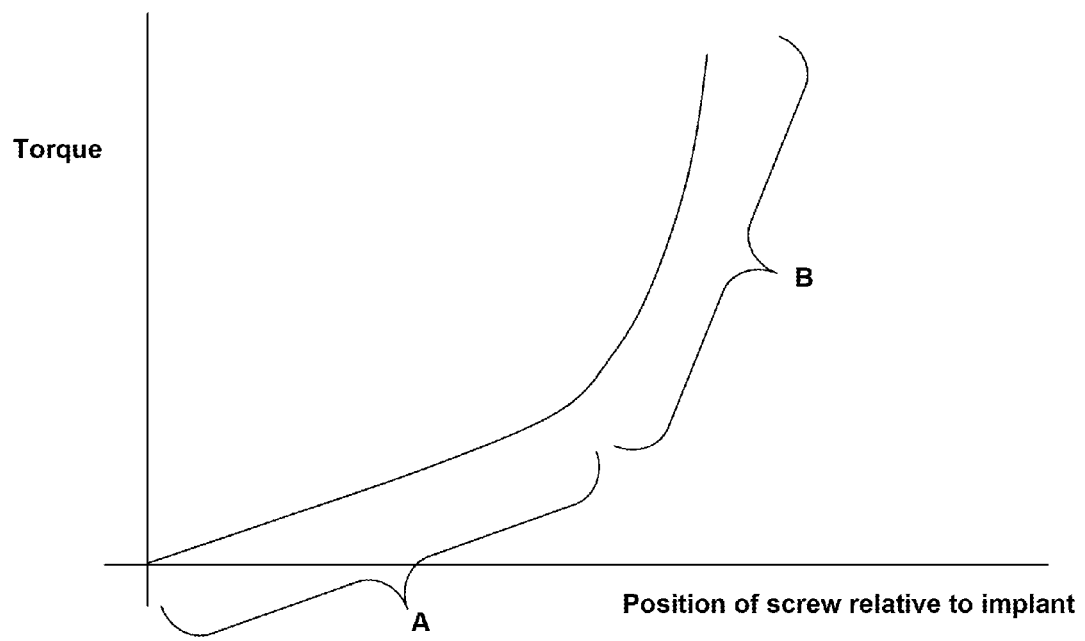
FIG. 9 is a graph illustrating how the torque needed to advance the screw varies as a function of position of the screw along the screw advancement path.
Figure 9:
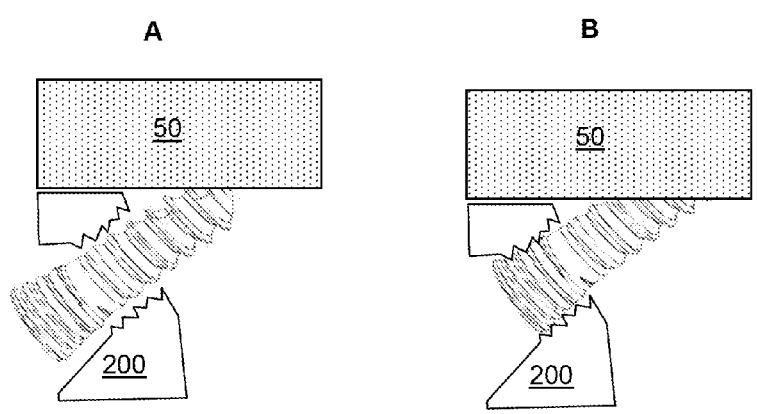

Referring now to FIG. 9, there is illustrated a relation of torque needed to advance the screw 300, as a function of position of the screw 300 relative to the anterior body 200 or more generally implant 10. In region A of FIG. 9, there is no contact between the screw thread 350 and the anterior body internal thread 220, so whatever torque is needed to advance the screw 300 results only from interaction of the screw 300 with bone 50, such as by friction. Such torque can be expected to slightly increase as the screw 300 advances into bone 50. In region B, the screw thread 350 contacts the anterior body internal thread 220, and as the screw 300 advances into bone 50 additional friction results from the taper of at least one of those threads. With proper design, it can be arranged that the torque in Region B is palpably different from the torque in Region A and also that the torque in Region B increases more rapidly (for example, two or three or more times more rapidly) as a function of advancing the screw position than is the case in Region A. This may especially be the case due to the taper that may exist on at least one of the screw hole internal thread 220 and the external thread 350. Thus, passage from region A into region B may be sensed in a tactile manner by the surgeon who is turning the screw.

It can be appreciated that various embodiments provide two different and independent methods of detecting or verifying that the screw 300 has been inserted to a proper position to achieve back-out prevention. One method is based on the torque characteristics as illustrated in FIG. 9, and the other method is the visual characteristics as illustrated in the contrast between FIG. 8A and FIG. 8B. Thus, an embodiment of the invention provides verifying or detecting the achievement of back-out prevention in two different independent ways.

Figure 10A:
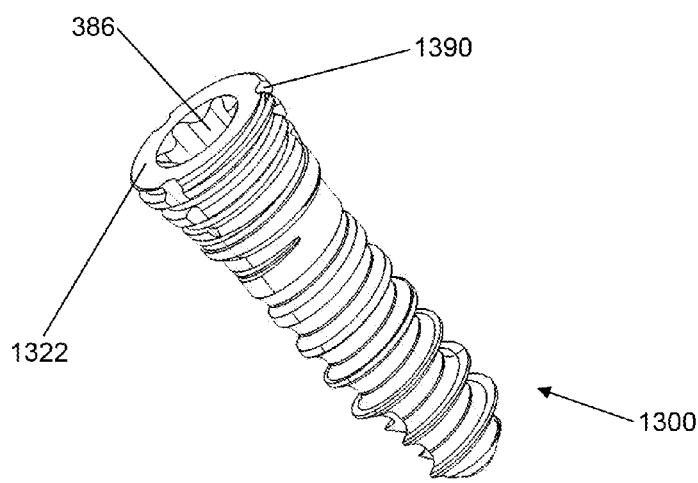
FIG. 10A is a perspective view of another embodiment of a screw.
Figure 10B:
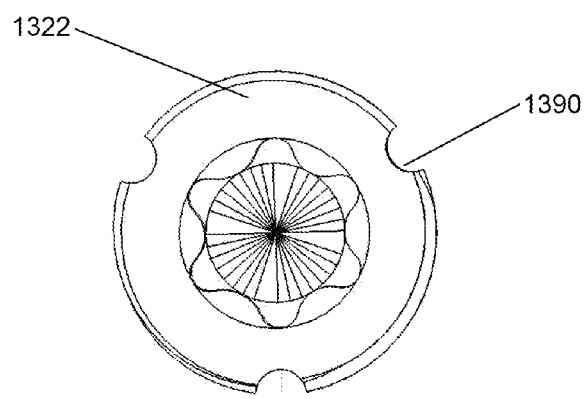
FIG. 10B is a top view of the screw of the embodiment shown in FIG. 10A.
Figure 11:
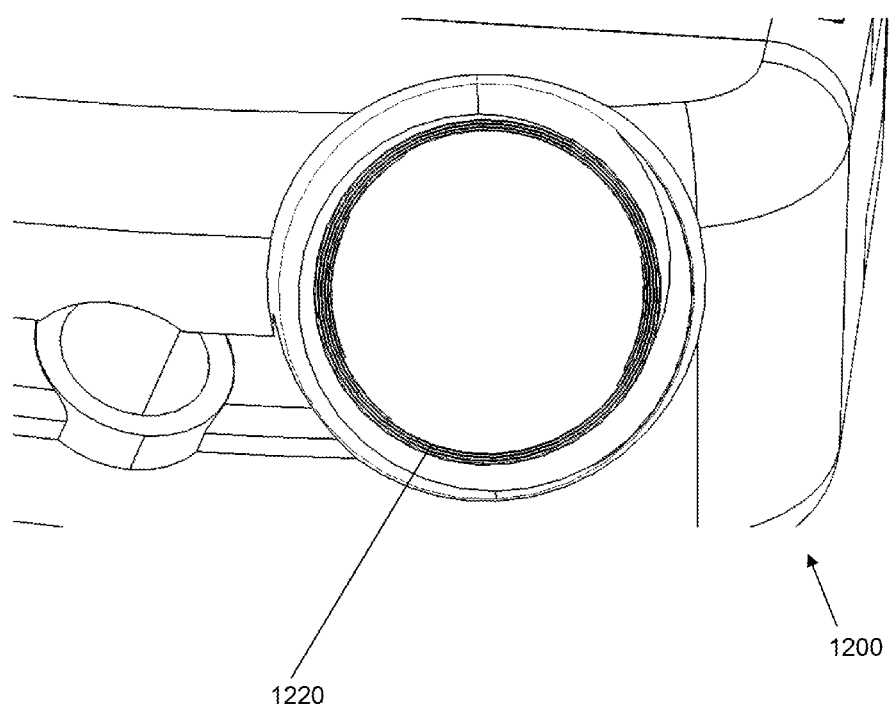
FIG. 11 is a perspective view of an anterior body and in particular the threads of that body.

Yet another embodiment is illustrated in FIGS. 10A, 10B, and 11. In this embodiment, the implant 10 may be provided with a posterior body 1100 and an anterior body 1200, with the anterior body 1200 having internal threads 1220. The internal threads 1220 may be helical threads that are substantially identical at various places around the helix, without a recess into the threads such as was provided in an earlier embodiment herein.

In this embodiment, the screw 1300 (FIGS. 10A and 10B) has a screw head 1322 and has at least one indentation 1390 at a periphery of the screw head 1322. As illustrated, there are three such indentations 1390. Aside from the presence of the indentation(s) 1390, the periphery of the screw head 1322 may possess at least one circular arc and may be substantially rounded. Despite the presence of the indentation(s) 1390, the screw head 1322 may be substantially rigid.

Referring now to FIG. 12A-12D, there are shown two different configurations and appearances of the screw head 1322 and nearby material of anterior body 1200, so as to provide a visual contrast between the appearance of a fully-inserted screw configuration and the appearance of a partially-inserted configuration.

Figure 12A:
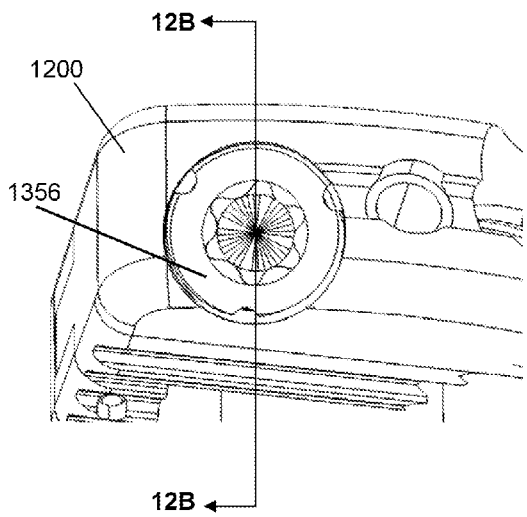
FIG. 12A is a perspective view of the screw head and the anterior body in a not-fully-engaged condition.
Figure 12B:
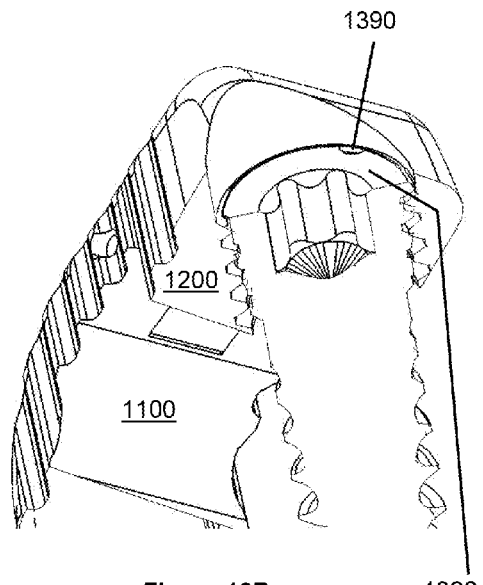
FIG. 12B is a perspective cross-section the embodiment shown in FIG. 12A.

In the partially-inserted configuration shown in FIG. 12A, the visible region 1356 may be something other than a perfect circle, such as a circle with one or more indentations 1390 in its outer periphery. As illustrated in FIG. 12A and more particularly in cross-section in FIG. 12B, the head 1322 of screw 1300 has not yet entered the threads 1220 in the anterior body 1200. Therefore, what is visible is the entire periphery of the head 1322 of screw 1300, including indentations 1390. In this configuration, the screw thread 1352 of the threaded region 1350 is only loosely engaged, if engaged at all, with the corresponding portion of the thread 1220.

Figure 12C:
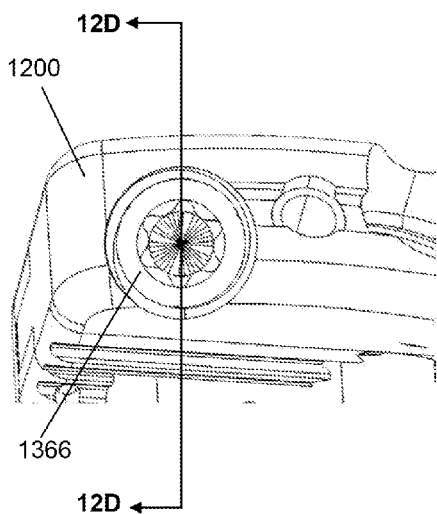
FIG. 12C is a perspective view of the screw head and the anterior body in a fully-engaged condition.
Figure 12D:
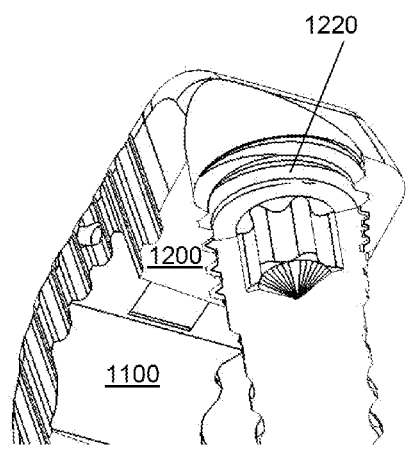
FIG. 12D is a perspective cross-section of FIG. 12C.
Figure 13:
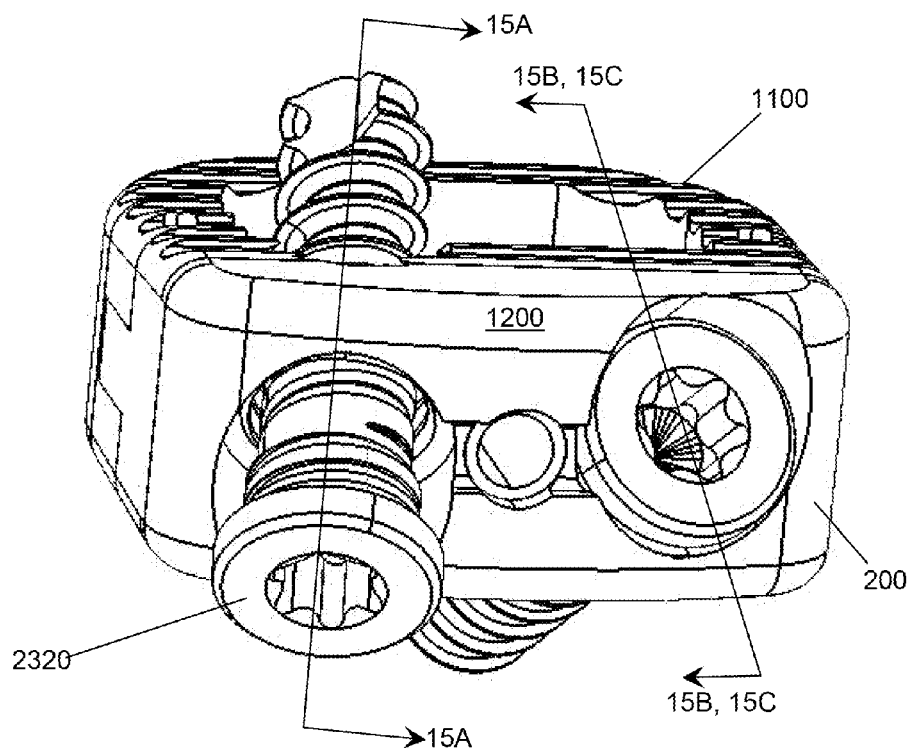
FIG. 13 is a perspective view of an assembly of another embodiment of the invention, having a hard-stop feature.
Figure 14:
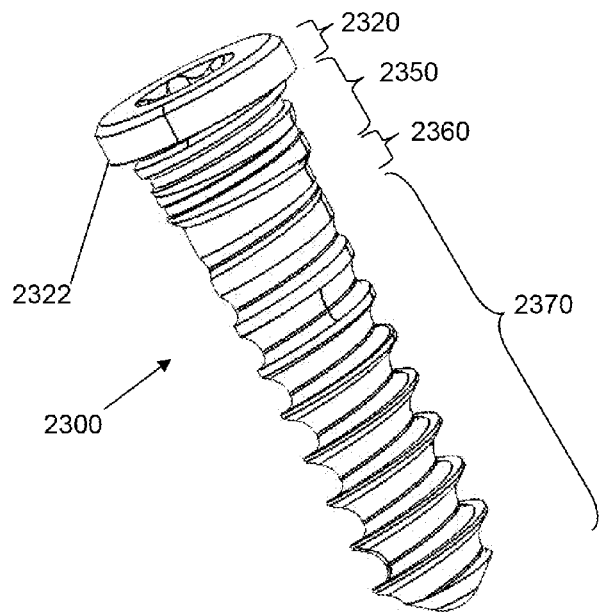
FIG. 14 is a perspective view of a screw shown in FIG. 13.

In the fully-inserted configuration shown in FIG. 12C, the visible region 1366 may be generally circular. In this configuration, the screw thread 1352 of the threaded region 1350 is tightly engaged with the corresponding portion of the thread 1220. As illustrated in FIG. 12C and more particularly in cross-section in FIG. 12D, the head 1322 of the screw 1300 has already entered the threads 1220 in the anterior body 1200, with the result that what is visible is a circular region defined substantially by the crests of the threads 1220, and indentations 1390 in head 1322 of screw 1300 are hidden within the threads 1220 and are not visible.

In a radial direction, the radial distance from the longitudinal axis of the screw 1300 to the radially-innermost point of indentation 1390, may be greater than the radial distance from the longitudinal axis of the hole 1320 to the crest of the thread 1220. In this way, when the screw 1300 is fully engaged with the anterior body 1200, the indentation 1390 can be "hidden" by the thread 1220.

It can be understood that although the posterior body 100 and the anterior body 200 have been described and illustrated as being distinct separate components joined to each other, it would also be possible to manufacture an implant 10 as a single unitary component. Such unitary component could be made of either polymer or metal, as desired.

It can be appreciated that the frictional back-out prevention can be accomplished if the external thread 350 is tapered whether or not the internal thread 220 is tapered. The internal thread 220 has been illustrated as being uniform in pitch and as having constant major diameter (other than having material partially cut away in certain places for recessed perimeter regions 261, 263). However, it is also possible that the internal thread 220 could be tapered in a way that corresponds at least approximately to the taper of the external thread 350, in a way that resembles threads used in pipe for conventional plumbing fittings. It can further be appreciated that frictional back-out prevention can be accomplished if the internal thread 220 is tapered while the external thread 350 is of constant diameter.

It can be appreciated that in regard to visual indication of engagement, there are also other possible visual shape changes other than those illustrated herein. For example, the visible shape of the screw head for non-engagement could be circular, while the visible shape of the screw head for engagement could more generally be any non-circular shape. The shape illustrated in FIG. 8C may be a shape that is particularly easy to distinguish from the non-fully-engaged shape, because of the presence of sharp corners in the engaged shape. Somewhat more generally, a shape of the visible screw head that indicates engagement of back-out prevention and is easily recognizable could be any shape such that (viewed from the outside of the shape) has convex curvature in some places on its perimeter and concave curvature in other places on its perimeter. For the shape illustrated in FIG. 8C, the places of convex curvature are the generally long generally circular arcs, and the places of concave curvature are the relatively sharp corners.

Still other non-circular shapes of the visible screw head are also possible in the engaged situation, such as an elliptical shape or shapes with other numbers of perimeter regions (other than the four perimeter regions illustrated herein). More generally, the visible shape during non-engagement may be circular, and the visible shape during engagement may be generally non-circular. Stated in yet another way, the visible shape during non-engagement may be the full outline shape of the screw head (with the full outline shape of the screw head possibly being circular but not necessarily being circular), and the visible shape during engagement may be a shape that is different from the full outline shape of the screw head.

In an alternate embodiment, the visible shape during non-engagement may be the full outline shape of the screw head such that the full outline shape of the screw head a modification of a circle with the modification being at least one recess, and the visible shape during engagement may be circular.

It has been illustrated that the posterior body 100 makes up a somewhat larger portion of the implant 10 than does the anterior body 200. However, in general, there could be any proportion between these two pieces. As mentioned elsewhere, it is also possible that the implant 10 could be made as a single piece.

The indentation 1390 could be any of various depths along the axis of the screw 1300. As illustrated, the indentations 1390 extend until there no longer is any intersection of the indentations 1390 with the thread 1350, but the axial extent of the indentations 1390 could be shorter if desired. The recess 261, 263 could be any of various depths along the axis of the screw 300. As illustrated, the recesses 261, 263 extend along the full length of the thread 220, but the axial extent could be partial if desired.

Of course, in the surgical environment, it is advantageous to provide contrasting shapes that are easily distinguishable from each other, because of issues of access space, lighting in the surgical field, and the presence of bodily fluids and nearby bodily tissue.

It may further be possible that a kit of parts provided for use by a surgeon may provide a "rescue" screw in addition to the nominal screw. The nominal screw may have a bone-engaging thread 370 whose maximum outside diameter is smaller than the inside diameter of the threads 220 of hole 210A, 210B, thereby allowing easy passage of the screw portion 370 through the hole 210A, 210B. It is further possible that the rescue screw may have a bone-engaging thread 372 whose maximum outside diameter is also smaller than the inside diameter of the threads 220 of hole 210A, 210B, but is larger than the maximum outside diameter of the nominal screw.

It can be noted that features described herein can be used in connection with cervical vertebrae, lumbar vertebrae and generally any vertebrae, and also can be used in application to bone fixation devices for use with bones other than vertebrae. Although the illustrations show an implant that possesses only two screws, embodiments of the invention can possess four screws, three screws, or in general any number of screws.

Features described herein can be used on all of the holes in the implant 10 that bone screws pass through, or they can be used on less than all of the holes that bone screws pass through. Features described herein could be used in combination with still other back-out prevention mechanisms, if desired.

An embodiment of the invention can also be described as a surgical method that uses any of the described devices.

Yet another embodiment is illustrated in FIGS. 13-15C. A screw 2300 may be provided having a hard stop feature such that when the screw 2300 is advanced sufficiently far with respect to the anterior body 200, the hard stop feature on the screw 2300 comes in contact with a corresponding feature on the anterior body 200, such that that contact substantially prevents any further advancement of the screw 2300 with respect to anterior body 200. The hard stop feature may provide a counter-bore 276 in the anterior body 200, with the counter-bore 276 having a flat bottom. The screw head 2320 may have a lip 2322 having a lip outside diameter. The screw 2300 may further be provided with a first threaded region 2350 and a second threaded region 2370, and optionally an unthreaded region 2360 between the first threaded region 2350 and the second threaded region 2370. As with the first threaded region 350 of the screw 300, it is possible that the first threaded region 2350 may be tapered so as to engage with the corresponding thread 220 of the anterior body 200 to produce friction preventing or resisting back-out of the screw 2320 from the anterior body 220. The lip 2322 may be located more proximally than any of the other features of the screw 2300. The outside diameter of the lip 2322 may be larger than the crest diameter of the thread of the screw 2300, or larger than the root diameter of the threads of the threaded region 2350 of the screw 2300. The lip 2322 may, as illustrated, have a lower (distal) surface that lies in a plane that is approximately perpendicular to a longitudinal axis of the screw 2300. However, other angles for the distal surface of the head 2320 are also possible, as long as they provide a hard stop by interaction with the anterior body 200.

The lip 2322 may cooperate with an internal feature of the anterior body 200 such as the counter-bore 276 to provide a hard stop that makes it substantially impossible for the screw 2300 to advance beyond a defined stop or limit. The lip 2322 may have an outside diameter that is larger than a corresponding dimension of a feature that the lip 2322 comes into contact with. Although planar features have been illustrated for the interfacing surfaces of lip 2322 and counter-bore 276, other shapes are also possible, such as frustoconical.

Figure 15A:
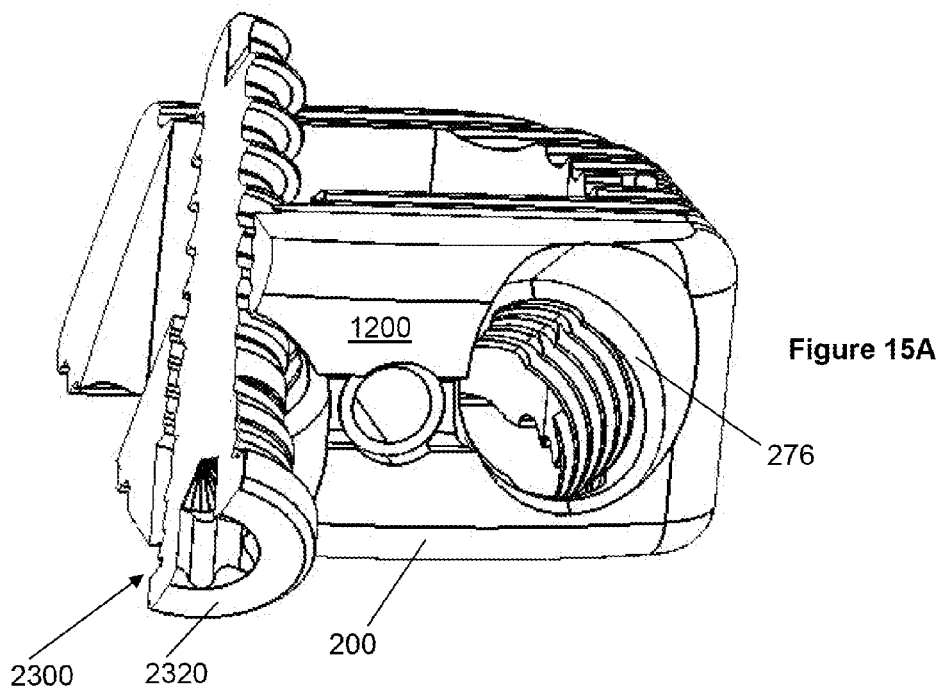
FIG. 15A is a perspective sectional view of the embodiment shown in FIG. 13, showing a screw that is only partially inserted into the implant assembly.
Figure 15B:
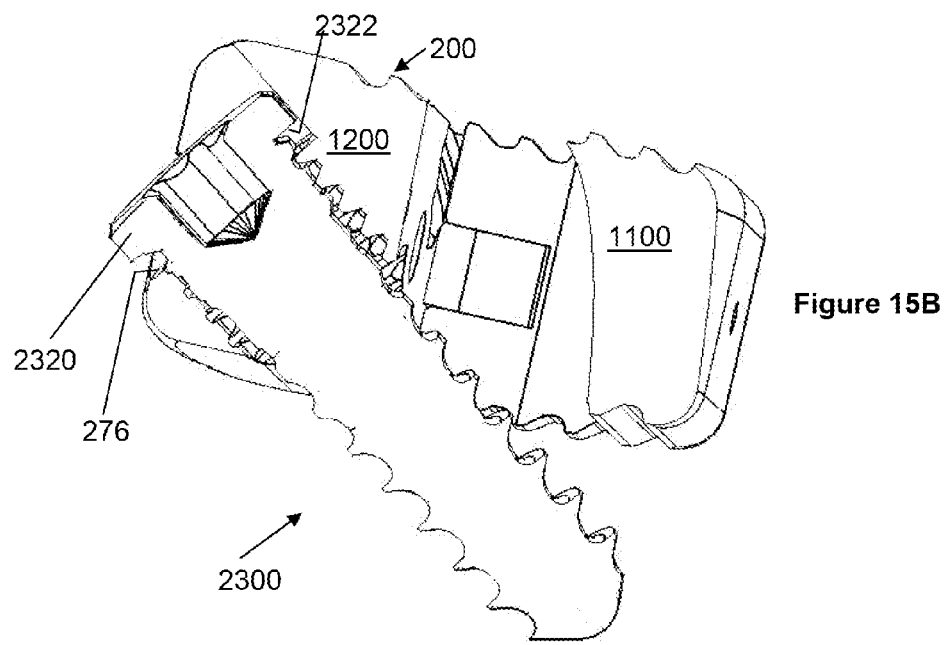
FIG. 15B is a perspective sectional view of the embodiment shown in FIG. 13, showing a screw that is more completely inserted into the implant assembly as compared to what is shown in FIG. 15A.
Figure 15C:
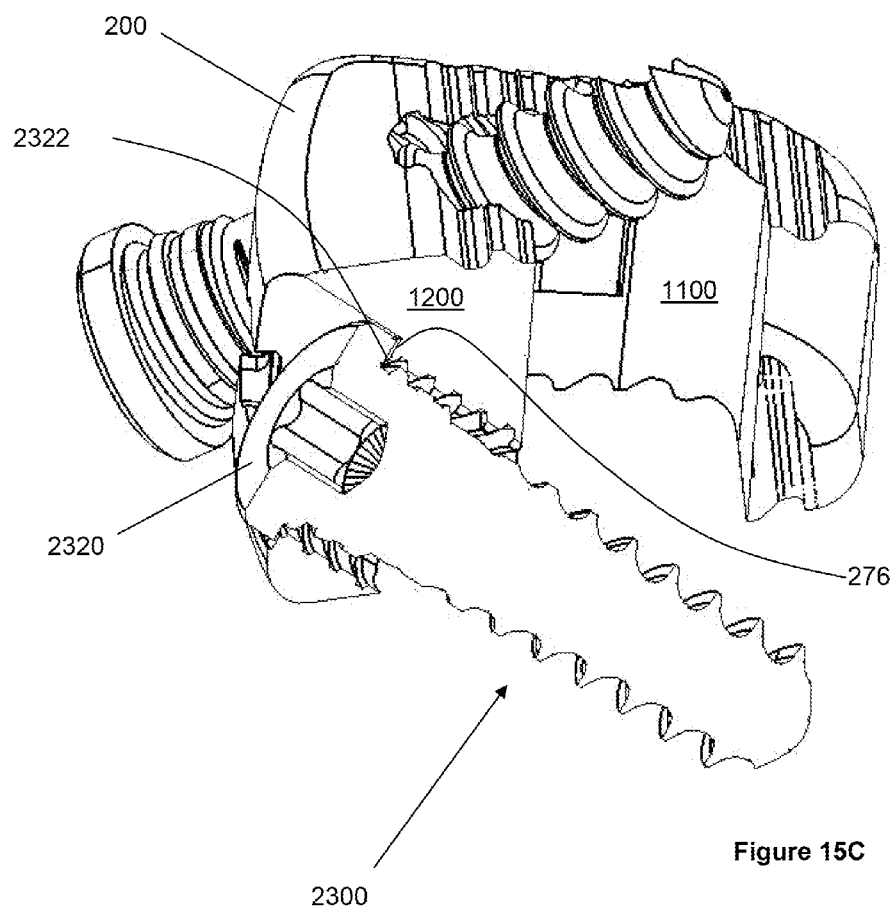
FIG. 15C is a perspective sectional view of the embodiment shown in FIG. 13, showing a screw that is completely inserted into the implant assembly.
Figure 16:
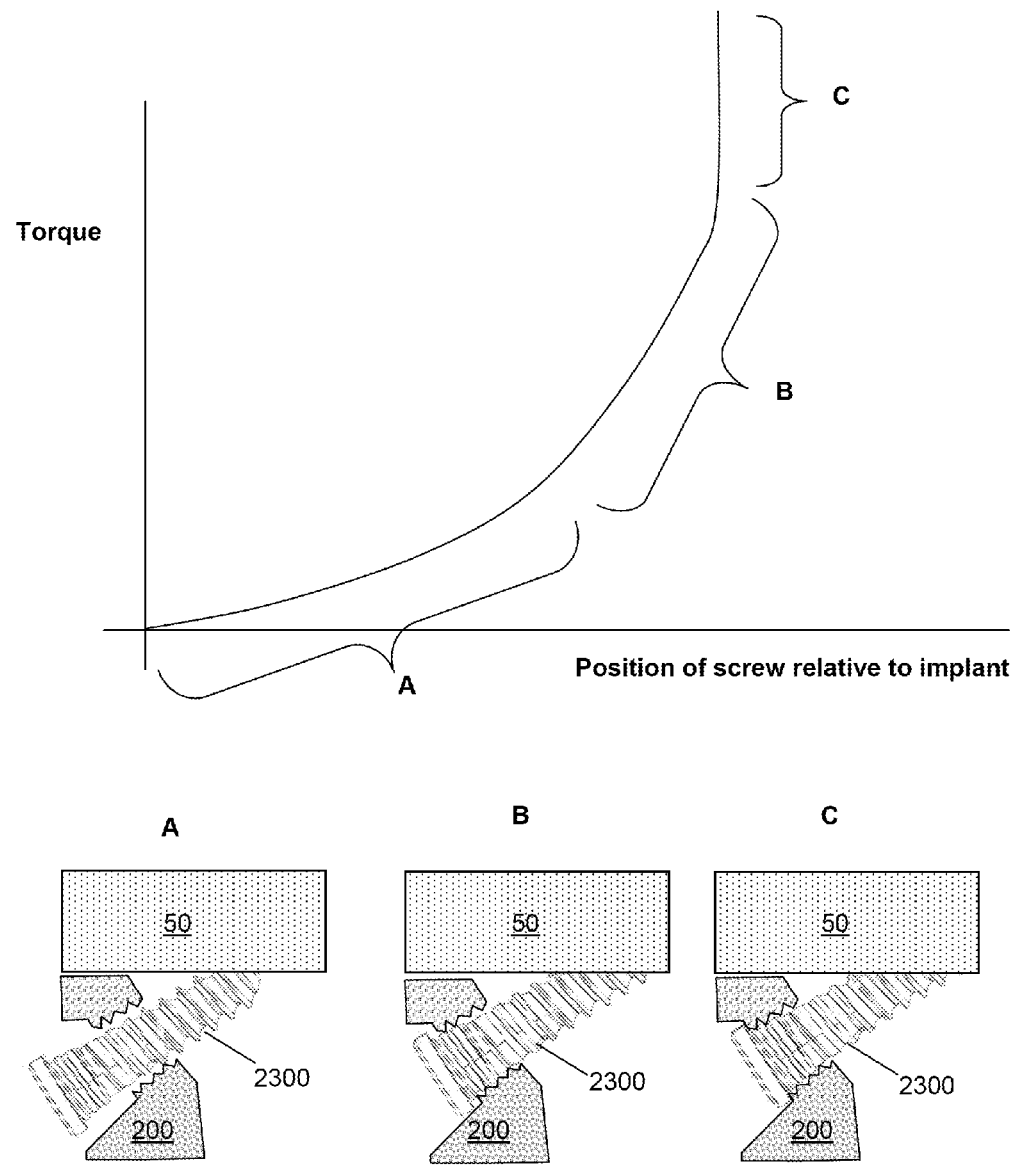
FIG. 16 is a graph illustrating how the torque needed to advance the screw varies as a function of position of the screw along the screw advancement path, for the embodiment shown in FIG. 13.

Various stages of interaction of the screw 2300 with the anterior body 200 are illustrated in FIGS. 15A-15C, and also in the pictorial portions of FIG. 16. In FIG. 15A, which depicts a screw that is only partially inserted into the implant assembly, the screw 2300 would interact with bone but the threads of region 2350 do not yet interact with the corresponding internal threads of anterior the body 200. In FIG. 15B, which depicts a screw that is further inserted into the implant assembly, the screw 2300 would again interact with bone but the threads of region 2350 also interact with the corresponding internal threads of the anterior body 200. FIG. 15C illustrates a configuration in which the lip 2322 directly contacts a corresponding facing feature of the anterior body 200. Such facing feature could be a counter-bore 276 having a flat bottom. FIGS. 15A, 15B and 15C also correspond to regions A and B and C as illustrated in FIG. 16.

The described features may result in a torque characteristic as illustrated in FIG. 16, which is a description of the relation of torque needed to advance the screw 2300, as a function of position of the screw 2300 relative to the anterior body 200 or more generally the implant 10. The characteristic illustrated in FIG. 16 has a first or "A" region similar to what was illustrated in FIG. 9, and a second or "B" region as also similar to what was illustrated in FIG. 9. Furthermore, when the screw 2300 has advanced to a defined location, FIG. 16 shows a third or "C" region such that it is simply not possible for the screw 2300 to advance beyond a defined limit with respect to the anterior body 200, no matter how much torque is applied to the screw 2300. As a result, in FIG. 16 the "C" region of the characteristic graph is substantially vertical. This is further illustrated in the pictorial portion of FIG. 16, for condition C, in which the lip 2322 directly contacts a corresponding feature of the anterior body 200 to form such a limit.

The foregoing description of structures and methods has been presented for purposes of illustration. It is not intended to be exhaustive or to limit the invention to the precise steps and/or forms disclosed, and obviously many modifications and variations are possible in light of the above teaching. Features described herein may be combined in any combination. Steps of a method described herein may be performed in any sequence that is physically possible. It is understood that while certain forms of a uniplanar screw have been illustrated and described, it is not limited thereto and instead will only be limited by the claims, appended hereto. All referenced documents are incorporated by reference herein.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The invention claimed is:

1. A spinal surgical device, comprising:
   an implant suitable to fit in an intervertebral space between adjacent vertebrae, said implant comprising a hole therethrough suitable to accept a screw; and
   wherein said hole comprises an interior envelope that is non-circular, and wherein at least a portion of said hole having an internal helical thread,
   in combination with a screw, wherein said screw has a first threaded region in a side surface of a head of said screw and has a second threaded region along a shaft of said screw, wherein when said screw head is screwed into said internal helical thread in said hole to a torque corresponding to full insertion, a top surface of said head of said screw is within a region of said hole that has said internal helical thread.

2. The apparatus of claim 1, wherein said interior envelope of said hole comprises, dispersed around its perimeter, a first perimeter region and a second perimeter region, wherein said first perimeter region is recessed to a greater radial dimension than a radial dimension of said second perimeter region, wherein said first perimeter region intersects said internal helical thread.

3. The apparatus of claim 1, wherein said hole further comprises an entry region adjacent to said internal helical thread, said entry region being unthreaded.

4. The apparatus of claim 1, wherein said internal helical thread is of uniform pitch and uniform major diameter everywhere that it exists.

5. The apparatus of claim 1, wherein said first perimeter region is recessed such that in said first perimeter region some of said internal helical thread remains.

6. The apparatus of claim 1, wherein said first perimeter region is recessed such that in said first perimeter region none of said internal helical thread remains.

7. The apparatus of claim 1, wherein said implant comprises a posterior body and an anterior body joined to said posterior body, and said hole passes at least through said anterior body.

8. The apparatus of claim 7, wherein said joining of said posterior body and said anterior body comprises a dowel pin that is an interference fit in one of said posterior body and said anterior body and is a clearance fit in the other of said posterior body and said anterior body.

9. The apparatus of claim 1, wherein said implant comprises an open space therethrough suitable to contain bone graft material.

10. The apparatus of claim 1, wherein said first threaded region has a tapered thread.

11. The apparatus of claim 1, wherein said first threaded region has a first threaded region thread pitch and said internal helical thread has an internal helical thread pitch equal to said first threaded region thread pitch.

12. The apparatus of claim 1, wherein said first threaded region has a first threaded region thread pitch and said second threaded region has a second threaded region thread pitch, and said first threaded region thread pitch and said second threaded region thread pitch are different from each other.

13. A spinal surgical device, comprising:
an implant suitable to fit in an intervertebral space between adjacent vertebrae, said implant comprising a hole therethrough;
said hole comprising a hole internal thread; and
a screw comprising a screw head and a screw shaft that is suitable to pass through said hole; and
wherein an interaction between said screw and said implant provides a back-out prevention feature for prevention of back-out of said screw from said implant; and
wherein said interaction of said screw and said implant provides a visual indication of engagement of said back-out prevention feature, said visual indication comprising a change in a shape of a visible portion of said screw head when said back-out prevention feature is engaged as compared to a shape of a visible portion of said screw head when said back-out prevention feature is not engaged.

14. The device of claim 13, wherein during non-engagement of said back-out prevention feature, said screw head is visible as a circular shape, and during engagement of said back-out prevention feature, said screw head is visible as a non-circular shape.

15. The device of claim 14, wherein during non-engagement of said back-out prevention feature, said screw head is visible as a full shape of said screw head, and during engagement of said back-out prevention feature, said screw head is visible as a non-circular shape.

16. The device of claim 14, wherein said non-circular shape comprises a more-compact region and a more-expanded region.

17. The device of claim 14, wherein said non-circular shape has a perimeter that comprises a convex portion and a concave portion.

18. The device of claim 13, wherein during non-engagement of said back-out prevention feature, said screw head is visible as a full shape of said screw head, said full shape being non-circular, and during engagement of said back-out prevention feature, said screw head is visible as a circular shape.

19. The spinal surgical device of claim 13, wherein during non-engagement of said back-out prevention feature, said visible portion of said screw head comprises at least one circular arc and at least one indentation along a periphery of said screw head.

20. The device of claim 19, wherein said indentation has a minimum radial position that is at a greater radius than a radius of a crest of said hole internal thread.

21. A spinal surgical device, comprising:
an implant suitable to fit in an intervertebral space between adjacent vertebrae, said implant comprising a hole therethrough, said hole having a hole internal thread; and
a screw comprising a screw head and a screw shaft suitable to pass through said hole; and
wherein a combination of said implant and said screw provides a back-out prevention feature for prevention of back-out of said screw from said implant,
wherein said back-out prevention feature provides both a visual indication of engagement of said back-out prevention feature and a torque indication of engagement of said back-out prevention feature;
wherein said visual indication comprising a change of a visible shape of the screw head; and
wherein said torque indication comprising a change in an amount of torque needed to advance said screw.

22. The device of claim 21, wherein said hole has an internal helical thread, and wherein said hole comprises, dispersed around its perimeter, a first perimeter region and a second perimeter region, wherein said second perimeter region is recessed to a greater radial dimension than a radial dimension of said first perimeter region.

* * * * *